United States Patent [19]

Sredni et al.

[11] Patent Number: 5,576,347
[45] Date of Patent: Nov. 19, 1996

[54] METHOD OF TREATING GASTRIC ULCERS

[76] Inventors: Benjamin Sredni, Shachal 3 Street, Kfar-Saba; Michael Albeck, 8 Harel Street, Ramat-Gan, both of Israel

[21] Appl. No.: 339,334

[22] Filed: Nov. 14, 1994

[51] Int. Cl.⁶ .................. A61K 31/35; A61K 31/335; A61K 31/095
[52] U.S. Cl. .................. 514/467; 514/450; 514/452; 514/460; 514/706; 514/927
[58] Field of Search .................. 514/450, 452, 514/460, 467, 706, 927

[56] References Cited

U.S. PATENT DOCUMENTS

4,929,739  5/1990  Sredni et al. .................. 549/347
5,126,149  6/1992  Sredni et al. .................. 424/650

*Primary Examiner*—Kimberly Jordan
*Attorney, Agent, or Firm*—Hedman, Gibson & Costigan, P.C.

[57] ABSTRACT

The invention is based on the use of a tellurium compound to treat or prevent gastritis or peptic ulcer. The tellurium compounds may be administered orally or parenterally to a host who is afflicted with or is susceptible to these conditions.

11 Claims, 5 Drawing Sheets

METHOD OF TREATING GASTRIC ULCERS

BACKGROUND OF THE INVENTION

The present invention provides a novel therapy for application to the treatment of gastritis and peptic ulcers.

Gastritis and peptic ulcers are commonly seen in clinical practice. The usual treatments for these conditions have been based on surgical intervention and/or the use of anticholinergic agents, antacids, H2 receptor blocking agents and more recently anti-infective agents.

Interleukin-1 (IL-1) has been described in the literature as having a potential gastroprotective effect against injury. Epidermal growth factor (EGF) has also been described as having ulcer healing activity.

SUMMARY OF THE INVENTION

The present inventors have discovered that certain selected tellurium compounds may be directly used for the treatment of gastritis or peptic ulcers or as an adjunct therapy for the treatment of gastric ulcers.

DETAILED DESCRIPTION OF THE INVENTION

The tellurium compounds for use in the invention include those of the formula:

wherein t is 1 or 0; u is 1 or 0; v is 1 or 0; R, $R_1$, $R_2$, $R_3$, $R_4$, $R_5$, $R_6$, $R_7$, $R_8$, and $R_9$ are the same or different and are independently selected from the group consisting of hydrogen, hydroxyalkyl of 1 to 5 carbons, hydroxy, alkyl or from 1 to 5 carbon atoms, halogen, haloalkyl of 1 to 5 carbon atoms, carboxy, alkylcarbonylalkyl of 2 to 10 carbons, alkanoyloxy of 1 to 5 carbon atoms, carboxyalkyl of 1 to 5 carbons atoms, acyl, amido, cyano, amidoalkyl of 1 to 5 carbons, N-monoalkylamidoalkyl of 2 to 10 carbons, N,N-dialkylamidoalkyl of 4 to 10 carbons, cyanoalkyl of 1 to 5 carbons alkoxy of 1 to 5 carbon atoms, alkoxyalkyl of 2 to 10 carbon atoms and —$COR_{10}$ wherein $R_{10}$ is alkyl of 1 to 5 carbons; and X is halogen; while the ammonium salt is illustrated, it is understood that other pharmaceutically acceptable salts such as K+ are within the scope of the invention. The compounds with the five membered rings are preferred.

As used herein and in the appended claims, the term alkyl of 1 to 5 carbon atoms includes straight and branched chain alkyl groups such as methyl; ethyl; n-propyl; n-butyl, and the like; the term hydroxyalkyl of 1 to 5 carbon atoms includes hydroxymethyl; hydroxyethyl; hydroxy-n-butyl; the term halkoakyl of 1 to 5 carbon atoms includes chloromethyl; 2-iodoethyl; 4-bromo-n-butyl; iodoethyl; 4-bromo-n-pentyl and the like; the term alkanoyloxy of 1 to 5 carbon atoms includes acetyl, propionyl, butanoyl and the like; the term carboxyalkyl includes carboxymethyl, carboxyethyl, ethylenecarboxy and the like; the term alkylcarbonylalkyl includes methanoylmethyl, ethanoylethyl and the like; the term amidoalkyl includes —$CH_2CONH_2$; —$CH_2CH_2CONH_2$; —$CH_2CH_2CH_2CONH_2$ and the like; the term cyanoalkyl includes —$CH_2CN$; —$CH_2CH_2CN$; —$CH_2CH_2CH_2CN$ and the like; the alkoxy, of 1 to 5 carbon atoms includes methoxy, ethoxy, n-propoxy, n-pentoxy and the like; the terms halo and halogen are used to signify chloro, bromo, iodo and fluoro; the term acyl includes $R_{16}CO$ wherein $R_{16}$ is H or alkyl of 1 to 5 carbons such as methanoyl, ethanoyl and the like; the term aryl includes phenyl, alkylphenyl and naphthyl; the term N-monoalkylamidoalkyl includes —$CH_2CH_2CONHCH_3$, —$CH_2CONHCH_2CH_3$; the term N,N-dialkylamidoalkyl includes —CH$_2$CON(CH$_3$)$_2$; CH$_2$CH$_2$CON(CH$_2$-CH$_3$)$_2$. The tellurium based compounds that are preferred include those of the formula:

and wherein X is halogen. The preferred halogen species is chloro.

Other compounds which are based on tellurium and may be used in the practice of the invention include PhTeCl$_3$, TeO$_2$ and TeX$_4$ ( C$_6$H$_5$)$_4$ P+(TeCl$_3$(O$_2$C$_2$H$_4$))—(Z. Naturforsh, 36, 307–312 (1981). Compounds of the following structure are also included:

Other compounds useful for the practice of invention include:

wherein R$_{11}$, R$_{12}$, R$_{13}$ and R$_{14}$ are independently selected from the group consisting of hydrogen, hydroxy-alkyl of 1–5 carbons atoms, hydroxy and alkyl of 1–5 carbons atoms.

Useful dihydroxy compounds for use in the preparation of compounds of structure A or B, include those of formula I wherein R, R$_1$, R$_4$ and R$_5$ are as shown in the Table:

TABLE $$HO-\underset{\underset{R_1}{|}}{\overset{\overset{R}{|}}{C}}-\underset{\underset{R_5}{|}}{\overset{\overset{R_4}{|}}{C}}-OH \qquad (I)$$

| R | R$_1$ | R$_4$ | R$_5$ |
|---|---|---|---|
| H | H | H | H |
| H | Cl | H | H |
| H | OCH$_3$ | H | H |
| H | COOCH$_3$ | H | H |
| H | H | CN | H |
| H | CHO | H | H |
| H | H | COOH | H |
| H | CH$_2$COOH | H | H |
| H | H | CH$_2$COOCH$_3$ | H |
| H | I | H | H |
| H | H | Br | H |
| H | H | CONH$_2$ | H |
| H | H | CH$_2$OH | H |

TABLE-continued $$HO-\underset{\underset{R_1}{|}}{\overset{\overset{R}{|}}{C}}-\underset{\underset{R_5}{|}}{\overset{\overset{R_4}{|}}{C}}-OH \qquad (I)$$

| R | R$_1$ | R$_4$ | R$_5$ |
|---|---|---|---|
| H | COOH | H | H |

Other dihydroxy compounds for use in the preparation of compounds A and B include those of formula II wherein R, R$_1$, R$_2$, R$_3$, R$_4$ and R$_5$ are as shown in the Table:

$$HO-\underset{\underset{R_1}{|}}{\overset{\overset{R}{|}}{C}}-\underset{\underset{R_3}{|}}{\overset{\overset{R_2}{|}}{C}}-\underset{\underset{R_5}{|}}{\overset{\overset{R_4}{|}}{C}}-OH \qquad (II)$$

| R | R$_1$ | R$_2$ | R$_3$ | R$_4$ | R$_5$ |
|---|---|---|---|---|---|
| H | H | H | H | H | H |
| H | H | Cl | H | H | H |
| H | CH$_2$OH | H | H | H | H |
| H | H | OH | H | H | H |
| H | H | H | CH$_3$ | H | H |
| H | H | H | CH$_2$Cl | H | H |
| H | H | H | COOH | H | H |
| H | H | H | CH$_2$COOH | H | H |
| H | H | H | CHO | H | H |
| H | H | H | H | H | CH$_2$CHO |
| H | H | CONH$_2$ | H | H$_2$ | CH$_3$ |
| H | H | H | CN | H | H |
| H | H | H | H | CH$_2$COHN$_2$ | H |
| H | H | H | COOCH$_3$ | H$_3$ | H |
| H | H$_3$ | OCH$_3$ | H | H | H |

Other dihydroxy compounds for use in making compound of formula A and B include those of formula III wherein R, R$_1$, R$_2$, R$_3$, R$_4$ and R$_5$ are as shown in the Table.

$$HO-\underset{\underset{R_1}{|}}{\overset{\overset{R}{|}}{C}}-\underset{\underset{R_3}{|}}{\overset{\overset{R_2}{|}}{C}}-\underset{\underset{R_5}{|}}{\overset{\overset{R_4}{|}}{C}}-\underset{\underset{R_9}{|}}{\overset{\overset{R_8}{|}}{C}}-OH \qquad (III)$$

| R | R$_1$ | R$_2$ | R$_3$ | R$_4$ | R$_5$ | R$_8$ | R$_9$ |
|---|---|---|---|---|---|---|---|
| H | H | H | H | H | H | H | H |
| H | H | Cl | H | H | H | H | H |
| H | H | H | H | Br | H | H | H |
| H | H | OCH$_3$ | H | H | H | H | H |
| H | H | CONH$_2$ | H | H | H | H | H |
| H | Br | H | H | H | H | H | H |
| H | H | H | H | CH$_2$COOH | H | H | H |
| H | H | Cl | Cl | H | H | H | H |
| H | CH$_2$COOH | H | H | H | H | H | H |
| H | H | CH$_3$ | H | H | H | H | H |
| H | CH$_3$ | H | H | H | H | H | H |
| H | CH$_2$Cl | H | H | H | H | H | H |
| H | H | H | I | H | H | H | H |
| H | CH$_2$CN | H | H | H | H | H | H |
| H | H | H | H | CH$_2$CH$_2$OH | H | H | H |

Additional dihydroxy compounds include those of formula IV wherein R, R$_1$, R$_2$, R$_3$, R$_4$ and R$_5$ are as shown in the Table.

$$\begin{array}{c} \phantom{HO-}R\phantom{-}R_2\phantom{-}R_4\phantom{-}R_6\phantom{-}R_8 \\ \phantom{HO-}|\phantom{-}|\phantom{-}|\phantom{-}|\phantom{-}| \\ HO-C-C-C-C-R-OH \\ |\phantom{-}|\phantom{-}|\phantom{-}|\phantom{-}| \\ R\phantom{-}R_3\phantom{-}R_5\phantom{-}R_7\phantom{-}R_9 \end{array} \quad (IV)$$

| R   | $R_1$        | $R_2$            | $R_3$ | $R_4$    | $R_5$      | $R_6$ | $R_7$       | $R_8$ | $R_9$ |
|-----|--------------|------------------|-------|----------|------------|-------|-------------|-------|-------|
| H   | H            | H                | H     | H        | H          | H     | H           | H     | H     |
| H   | H            | Cl               | H     | H        | H          | Cl    | H           | H     | H     |
| H   | H            | Cl               | Cl    | H        | H          | H     | H           | H     | H     |
| H   | H            | CONCH$_3$        | H     | H        | H          | Br    | H           | H     | H     |
| H   | H            | Br               | H     | H        | H          | CON(CH$_3$)$_2$ | H | H     | H     |
| H   | H            | H                | OCH$_3$ | H      | H          | H     | H           | H     | H     |
| H   | H            | H                | H     | OCH$_3$  | H          | H     | H           | H     | H     |
| H   | H            | H                | H     | CH$_2$COOH | H        | H     | H           | H     | H     |
| H   | H            | COOH             | H     | H        | H          | H     | H           | H     | H     |
| H   | CH$_3$       | H                | H     | H        | H          | H     | H           | H     | H     |
| CH$_3$ | H         | H                | H     | H        | CH$_3$     | H     | H           | H     | H     |
| H   | CH$_2$CH$_3$ | H                | H     | H        | H          | H     | Cl          | H     | H     |
| H   | CH$_2$CN     | H                | H     | CH$_2$OH | H          | H     | H           | H     | H     |
| H   | H            | H                | I     | H        | H          | H     | H           | CN    | H     |
| H   | CH$_2$CH$_2$COOH | H            | H     | H        | H          | H     | H           | H     | H     |
| H   | H            | CHO              | H     | H        | H          | H     | H           | H     | H     |
| H   | H            | H                | F     | H        | H          | H     | H           | H     | H     |

Compounds of the following formula are also included:

$$\begin{array}{c} R_{15} \\ | \\ R_{16}-Te-R_{18} \\ | \\ R_{17} \end{array}$$

herein $R_{15}$, $R_{16}$, $R_{17}$ and $R_{18}$ are independently selected from halogen, alkyl of 1–5 carbons; aryl, acyl of 1–5 carbon hydroxyalkyl of 1–5 carbons and aminoalkyl of 1–5 carbons may be made by reacting the appropriate di, tri or tetrahaloselenide or telluride with the appropriate hydroxy compound which may be of the formula: HO—$R_{19}$; wherein $R_{19}$; is alkyl of 1 to 5 carbons, haloalkyl of 1 to 5 carbons, aryl, alkylaryl, alkylamido of 1 to 5 carbons, alkylcarbonyl of 1 to 5 carbons, cyanoalkyl of 1 to 5 carbons, cyanoalkyl of 1 to 5 carbons, and an alkoxyalkyl of 2 to 10 carbons. Specific examples of $R_{16}$ include methyl, ethyl, n-propyl, phenyl, tolyl, amidoethyl, cyanomethyl, methyloxymethyl and CH$_2$CH$_2$COOH.

These compounds are described in U.S. Pat. No. 4,761,490 which is incorporated by reference. In addition, TeCl$_4$; TeBr$_4$ and compounds which give in aqueous solution TeO$_2$ preferably in the form of a complex such as for example TeO$_2$ complex with citric acid or ethylene glycol.

For the prevention and treatment of gastritis and peptic ulcer, the tellurium compound may be administered by the oral, intramuscular, intravenous, transdermal or intraperitoneal route to mammals including humans. The oral dose will be 0.15 to 0.5 mg/kg of body weight daily and preferably from 0.03 to 0.1 mg/kg of body weight daily in one dose or in divided doses. The parenteral dose will be 0.03 to 0.2 mg/kg of body weight daily and preferably from 0.006 to 0.02 mg/kg daily given as a bolus injection or as a continuous parenteral infusion.

The invention also includes the prevention of gastritis and peptic ulcers when hydrochloric acid or hydrochloric acid precursors are administered in the treatment of achlorhydria. In addition, the tellurium compounds may be administered concomitantly with non-steroidal anti-inflammatory drugs (NSAIDS) such as acetylsalicylic acid, pirooxicam, naproxen and indomethacin to prevent erosion of the gastric mucosa and subsequent ulcer formation by the administration by the oral, intramuscular, intravenous, transdermal or intraperitoneal route to mammals including humans, of an effective amount of a tellurium compound which is sufficient to prevent gastritis and or peptic ulcers.

DESCRIPTION OF THE PREFERRED EMBODIMENTS

EXAMPLE 1

Sprague-Dawley rats, 120–160 g. and Balb-C mice, 18–22 g. both male and female were used to confirm the activity of ammonium trichloro (O,O'-dioxoethylene tellurate).

The mucosal lesions were produced by intragastric (i.g.) instillation of 1 ml of 0.6N hydrochloric acid in each anesthetized rat. One hour later the animals were sacrificed and the stomachs were removed and filled with 100% formalin and were stored at room temperature to fix the mucosa with formalin. Then the stomachs were opened by incision and the size of the mucosal erosion was measured to determine the length along the largest width.

Five petechiae were considered to be the equivalent of a 1 mm lesion. The sum of the lesion lengths, from each animal, was expressed as the Ulcer Index according to Cho, British J. Pharmacol. 92:31–37 (1987). In tests to evaluate the effect of the tellurium compound on the healing of an ulcer, the ulcer was observed 24 hours after the administration of the tellurium compound which was given 1 hour after the i.g. administration of hydrochloric acid. In addition, when indomethacin instead of HCl was used to induce a gastric ulcer in a rat, 20 mg/kg of IND was administered i.g., followed by observation of the ulcer 6 hours later. To test the ammonium trichloro (O,O'-dioxoethylene tellurate) in mice, each mouse was treated with 0.15 ml of 0.6N HCl and the presence of the ulcer was confirmed by removal of a sample of the gastric mucosa which is examined with a microscope. The mucosal lesions were graded in different groups of mice according to the severity of lesions and accompanying bleeding as follows: (−): no lesions; (+) mild lesions (a few petechiae of ulcer or superficial ulcers); (++): moderately severe lesions (many deep ulcers); (+++) severe ulcers (more deep ulcers with bleeding).

The technique that was utilized for tissue extraction of PGs from gastric mucosa by Whitrle, J. Pharm Pharmacol 30, 467–468 (1978) was used with modification. At various times following i.g. instillation of the hydrochloric acid, the rats were sacrificed by an overdose of ether. The stomachs were quickly excised and the nonglandular portion was discarded. The remaining glandular portion was cut open along the lesser curvature. The oxyntic mucosa was scraped from the musculature and rinsed in a homogenizing buffer containing tris(hyroxymethyl) aminomethane hydrochloride 0.01M (pH7.4), sucrose 0.025M, dithiothreitol 1 mM and IND 50 μl. The sample was weighed and homogenized in 1 ml of the buffer for 1 minute in an homogenizer and 6 ml of cold acetone (−20° C.) was added to the homogenate, which was centifugerd at 1,500 rpm for 7 minutes. The precipitate was discarded and 4 ml of petroleum ether was added to the supernatant which was then shaken for 30 seconds and left still until two phases appeared. The upper phase containing petroleum ether was discarded.

The lower aqueous phase was acidified to pH 3.4, extracted with 6 ml of ethyl acetate and allowed to stand until two phases separated. The lower phase was discarded and the upper phase was evaporated with nitrogen gas to get rid of the ethyl acetate. The residue adherent to the wall of the tube was dissolved with 0.5 ml phosphate buffer supplied in the PGE2 enzyme immunoassay kit (EIA) (Pharmatest) and kept at −20° C. until the determination was carried out. Rat peritoneal exudate cells (PEC) were obtained by elicitation with 3% thioglycolate for 2 days and were incubated at $4 \times 10^6$/ml in RPMI-1640 medium enriched with 10% fetal serum for 2 hours to allow adherence. The adherent cells, most of which were considered macrophages, were treated with different concentrations of ammonium trichloro (O,O'-dioxoethylene tellurate) or only the reagent vehicle for 24 hours. The supernatants were collected and kept at −20° C. until the determinations were made. PGE2 was measured by EIA according to the manufacturers specification. Sample PGE2 was expressed as ng/g of gastric mucosa or ng/g of cell supernatants.

The method for extracting gastric EGF is a modified method based on the method described by Okita, et al., Drug Identification, No. 2, Supp 1, pp 13–17 (1990). At various times after i.g. instillation of hydrochloric acid, the mice were killed by cervical dislocation, the stomach was removed, the non-glandular portion discarded and the glandular portion was immediately frozen in liquid nitrogen, then weighed, homogenized by ultrasound (polytron) with 3×(v/w)? acetate buffer (0.05 mol/l) and centrifuged at 3000 rpm at 4° C. for 30 minutes. The supernatant was kept at −20° C. until the determination was made using [$I^{125}$] mouse EGF (mEGF) reagent pack for radioimmunoassay (Amersham) to measure the gastric EGF level of the mice. Radioassay was performed according to manufacturer's specification. Sample mEGF was expressed as ng/g tissue weight.

The group means were compared using the Student's two tailed t-test. All values were expressed as standard mean error. P levels of less than 0.05 were considered significant. For analysing the ulcer grading in mice, the Chi square test was employed.

Three escalating doses of 0.25, 0.5 and 1 mg/kg of ammonium trichloro (O,O'-dioxoethylene tellurate) were administered intraperitoneally to rats 2 hours prior to the challenge with hydrochloric acid. The ulcer index was inhibited by 12.7%, 68.8% and 70.3% at the respective doses set forth above. A mouse gastric ulcer model was developed in Balb/c mice by oral instillation with 0.15 ml of 0.6N hydrochloric acid. Lower grades and incidences of gastric lesions were seen in pretreated mice that were given different doses of ammonium trichloro (O,O'-dioxoethylene tellurate) as shown in Table 1.

Figure 1:
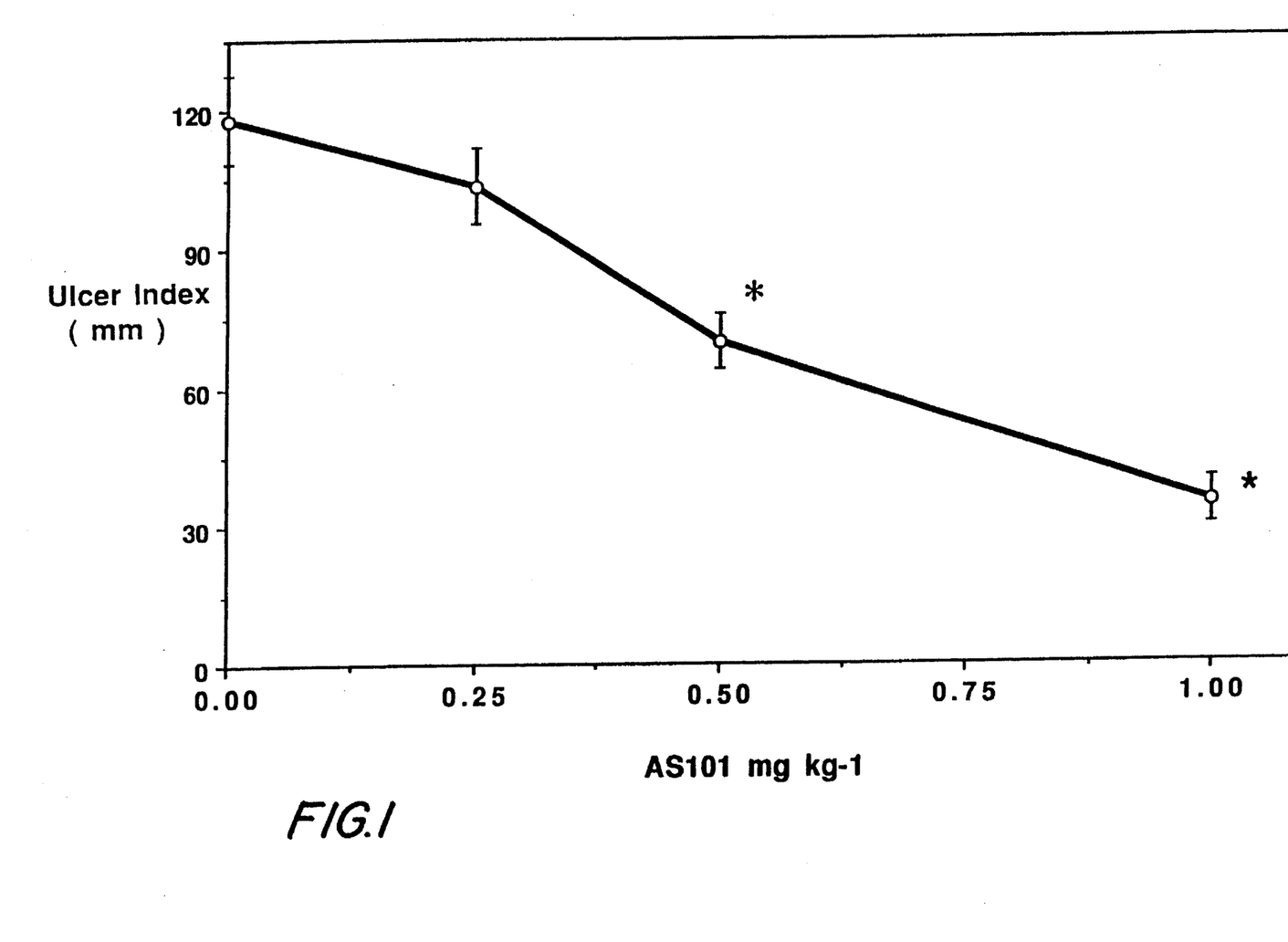
FIG. 1 is a graph which shows the protective effect of a particular tellurium compound in preventing a hydrochloric acid induced gastric ulcer in rats.
Figure 2:
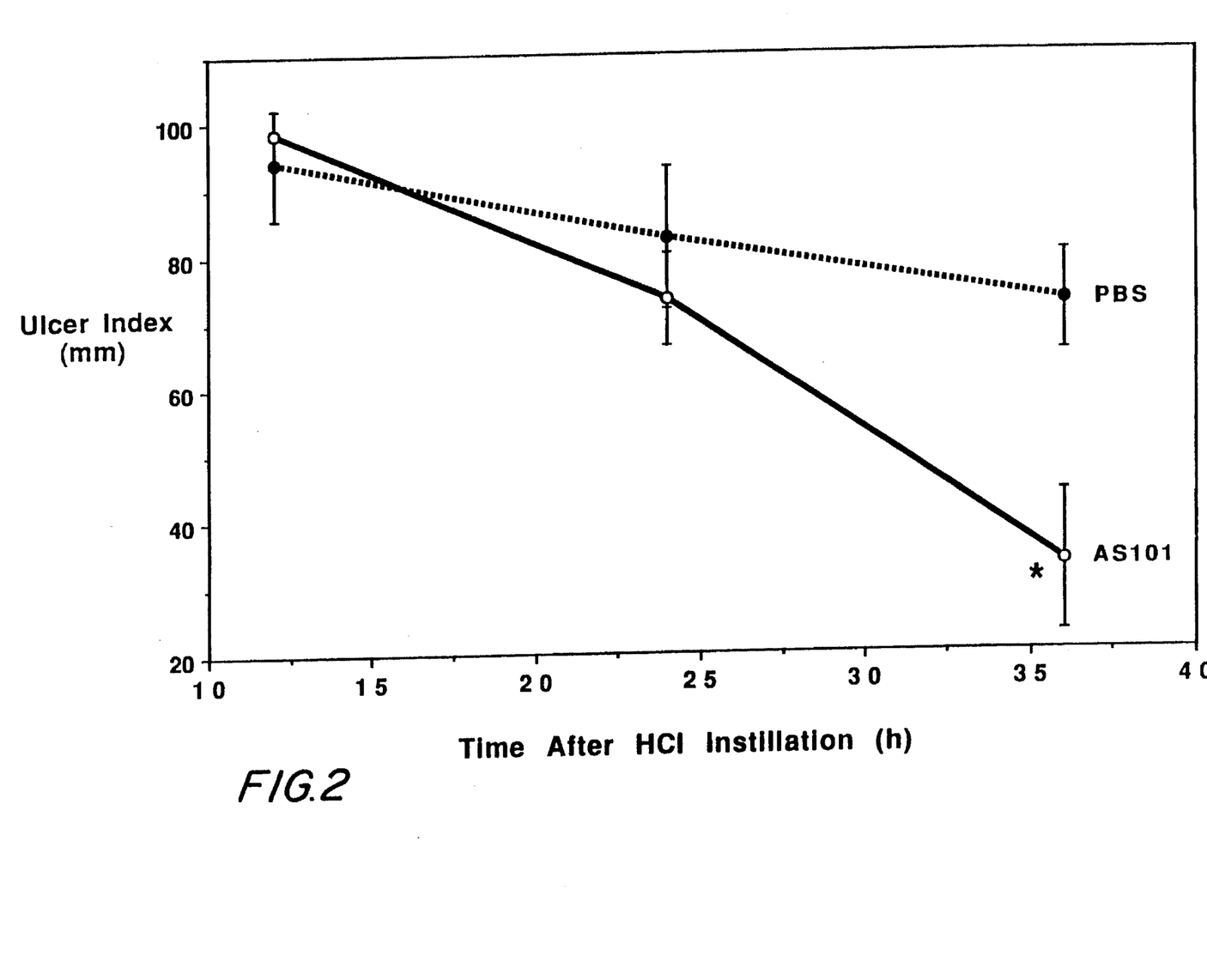
FIG. 2 is a graph which shows the acceleration of the healing of a hydrochloric acid induced gastric ulcer which is induced by a tellurium compound.
Figure 3:
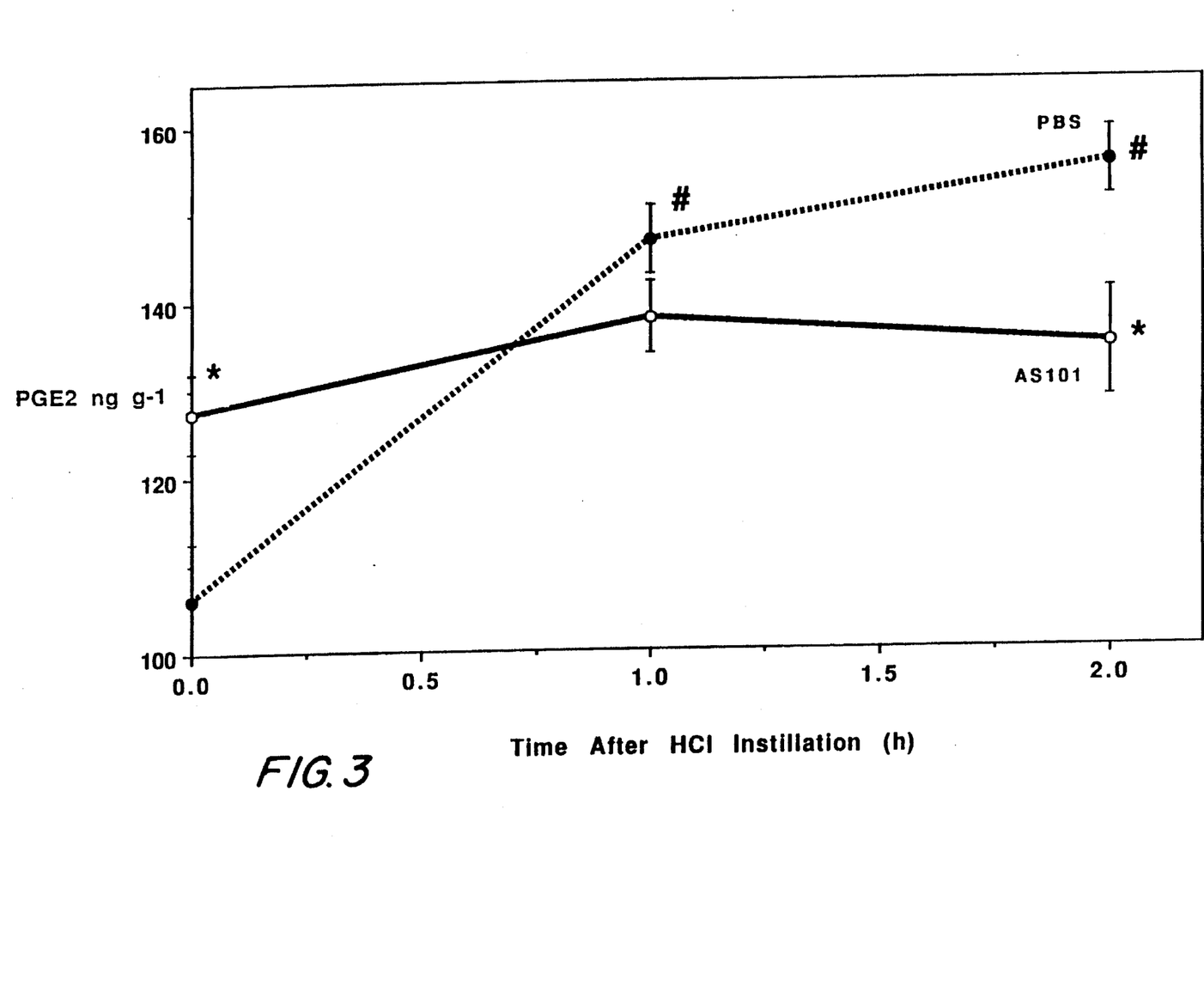
FIG. 3 is a graph which shows the effect of a tellurium compound on the PGE2 level in the gastric mucosa of rats that have been treated with hydrochloric acid.
Figure 4:
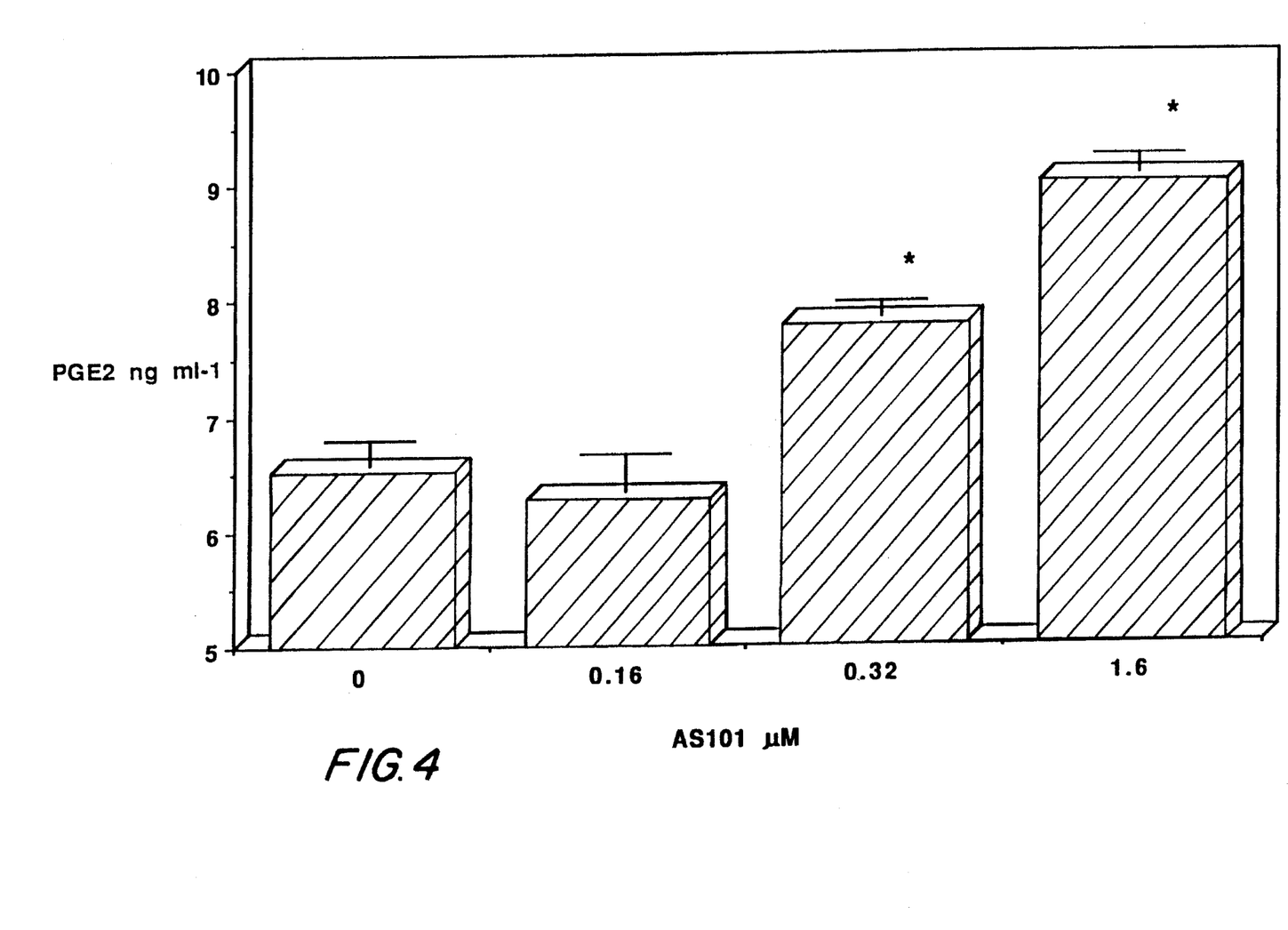
FIG. 4 is a graph which shows the effect of a tellurium compound on the induction of PGE2 from cultured rat peritoneal macrophages.
Figure 5:
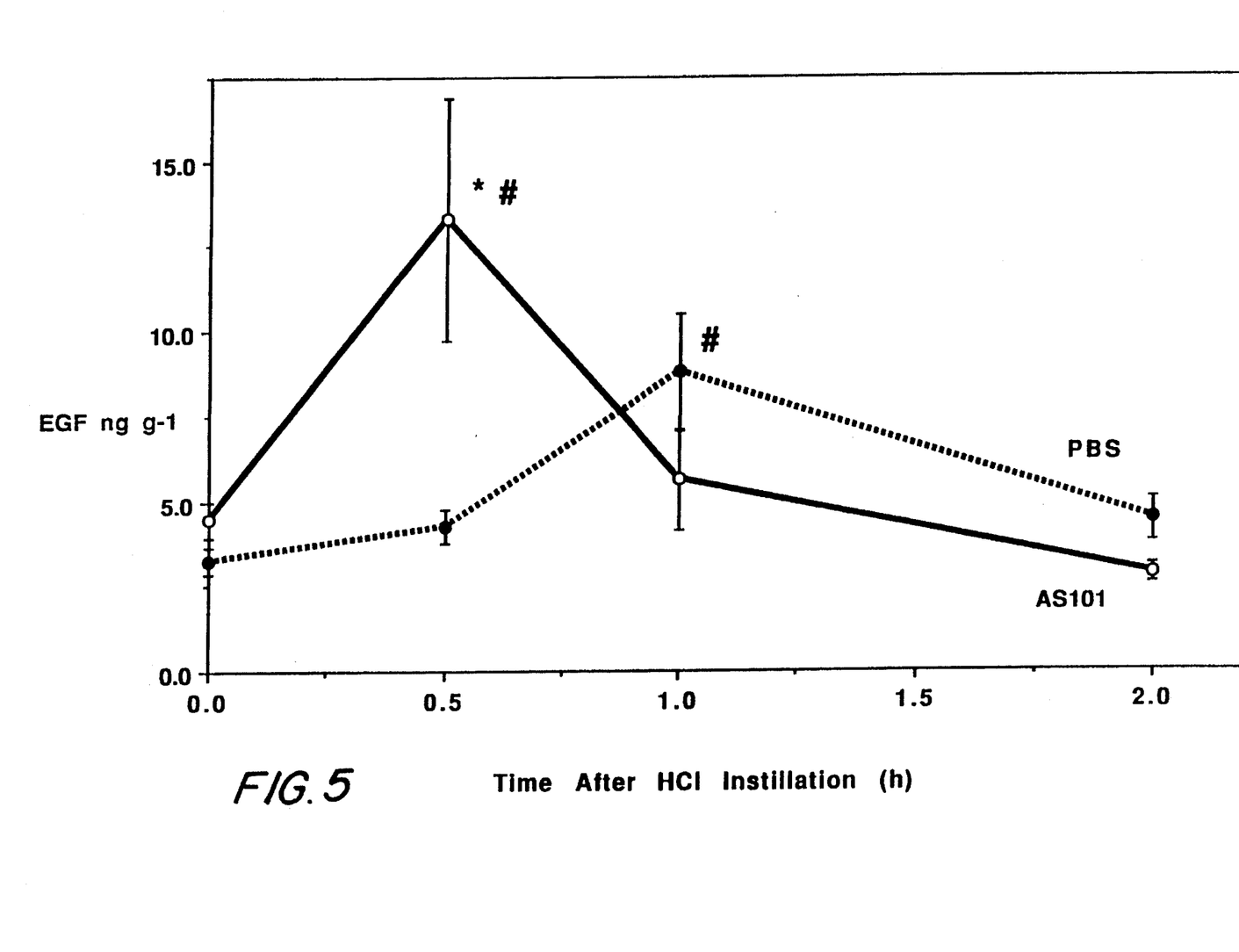
FIG. 5 is a graph which shows the effect of a tellurium compound on the level of gastric EGF in hyrdochloric acid treated rats.

In order to determine if ammonium trichloro (O,O'-dioxoethylene tellurate) exerts an anti-ulcer effect by directly affecting the gastric mucosa, two hours prior to hydrochloric acid instillation, rats were pretreated with ammonium trichloro (O,O'-dioxoethylene tellurate) at a dose 1 mg/kg in PBS or as a powder. The ulcer indices were recorded 1 hour after hydrochloric acid challenge as 115.0±5.36 mm, 85±7.3 mm and 89.7±8.7 mm. PBS and ammonium trichloro (O,O'-dioxoethylene tellurate) pretreated rats showed that rats that had hydrochloric acid instilled i.g. showed reduced ulcer indices compared to non-pretreated rats (P<0.05, P<0.01, respectively) but there was no significant difference between the two pretreated groups (P=0,743). Since the healing of the ulcer in of greater significance, two groups of rats were treated with ammonium trichloro (O,O'-dioxoethylene tellurate) or PBS respectively i.p. 1 hour after hydrochloric acid challenge. The results were observed 12, 24 and 36 hours later to assess if ammonium trichloro (O,O'-dioxoethylene tellurate) influences the healing of gastric ulcer. The results as reported in FIG. 3 showed that ammonium trichloro (O,O'-dioxoethylene tellurate) induced the healing of the experimentally induced gastric ulcer.

We claim:

1. A method for treating gastritis which is induced by hydrochloric acid, a hydrochloric acid precursor or a non-steroidal anti-inflammatory agent, or peptic ulcers which comprises administering to a host an effective amount of a tellurium compound of the formula:

(A)

(B)

or

TeO$_2$ or complexes of TeO$_2$ or

PhTeCl$_3$ (D)

or (C$_6$H$_5$)$_4$ P+(TeCl$_3$(O$_2$C$_2$H$_4$))—TeX$_4$, wherein; t is 1 or 0; u is 1 or 0; v is 1 or 0; R, R$_1$, R$_2$, R$_3$, R$_4$, R$_5$, R$_6$, R$_7$, R$_8$, and R$_9$ are the same or different and are independently selected from the group consisting of hydrogen, hydroxyalkyl of 1 to 5 carbons, hydroxy, alkyl of 1 to 5 carbon atoms, halogen, haloalkyl of 1 to 5 carbon atoms, carboxy, alkylcarbonylalkyl of 2 to 10 carbons, alkanoyloxy of 1 to 5 carbon atoms, carboxyalkyl of 1 to 5 carbons atoms, acyl, amido, cyano, amidoalkyl of 1 to 5 carbons, N-monoalkylamidoalkyl of 2 to 10 carbons, N,N-dialkylamidoalkyl of 4 to 10 carbons, cyanoalkyl of 1 to 5 carbons alkoxy of 1 to 5 carbon atoms, alkoxyalkyl of 2 to 10 carbon atoms and —$COR_{10}$ wherein $R_{10}$ is alkyl of from 1 to 5 carbons; and X is halogen and complexes thereof.

2. A method as defined in claim 1 wherein the tellurium compound is administered to a host who has a peptic ulcer.

3. A method as defined in claim 1 wherein the tellurium compound is administered to a host who is afflicted with gastritis.

4. A method as defined in claim 1 wherein the tellurium compound is ammonium trichloro (O,O'-dioxoethylene tellurate).

5. A method as defined in claim 2 wherein the tellurium compound is ammonium trichloro (O,O'-dioxoethylene tellurate).

6. A method as defined in claim 3 wherein the tellurium compound is ammonium trichloro (O,O'-dioxoethyele tellurate).

7. A method as defined in claim 1 wherein the tellurium compound is administered parenterally.

8. A method as defined in claim 1 wherein the tellurium compound is administered orally.

9. A method for treating gastritis or peptic ulcers which comprises administering to a host an effective amount of a tellurium compound of the formula:

(A)

or (B)

or $TeO_2$ or complexes of $TeO_2$ or $PhTeCl_3$ (D)

or $(C_6H_5)_4 P+(TeCl_3(O_2C_2H_4))$—$TeX_4$, wherein t is 1 or 0; u is 1 or 0; v is 1 or 0; R, $R_1$, $R_2$, $R_3$, $R_4$, $R_5$, $R_6$, $R_7$, $R_8$, and $R_9$ are the same or different and are independently selected from the group consisting of hydrogen, hydroxyalkyl of 1 to 5 carbons, hydroxy, alkyl of 1 to 5 carbon atoms, halogen, haloalkyl of 1 to 5 carbon atoms, carboxy, alkylcarbonylalkyl of 2 to 10 carbons, alkanoyloxy of 1 to 5 carbon atoms, carboxyalkyl of 1 to 5 carbons atoms, acyl, amido, cyano, amidoalkyl of 1 to 5 carbons, N-monoalkylamidoalkyl of 2 to 10 carbons, N,N-dialkylamidoalkyl of 4 to 10 carbons, cyanoalkyl of 1 to 5 carbons alkoxy of 1 to 5 carbon atoms, alkoxyalkyl of 2 to 10 carbon atoms and —$COR_{10}$ wherein $R_{10}$ is alkyl of from 1 to 5 carbons; and X is halogen.

10. A method as defined in claim 9 wherein the $TeO_2$ is complexed with citric acid.

11. A method as defined in claim 9 wherein the tellurium compound is ammonium trichloro (O,O'-dioxoethylene tellurate).

* * * * *